United States Patent [19]

Sayo et al.

[11] Patent Number: 5,581,007
[45] Date of Patent: Dec. 3, 1996

[54] PROCESS FOR PREPARING OPTICALLY ACTIVE ALLOPHENYLNORSTATIN DERIVATIVES

[75] Inventors: Noboru Sayo; Tetsuro Yamasaki; Hidenori Kumobayashi; Yoshifumi Yuasa; Tsukasa Sotoguchi, all of Kanagawa, Japan

[73] Assignee: Takasago International Corporation, Tokyo, Japan

[21] Appl. No.: 609,619

[22] Filed: Mar. 1, 1996

[30] Foreign Application Priority Data

Mar. 1, 1995 [JP] Japan ................... 7-041791

[51] Int. Cl.$^6$ .................. C07F 7/08; C07F 7/10
[52] U.S. Cl. ............. 556/418; 556/419; 560/23; 562/444
[58] Field of Search ................. 556/418, 419; 560/23; 562/444

[56] References Cited

U.S. PATENT DOCUMENTS 5,516,926  5/1996  Kim et al. .................. 556/418
5,516,927  5/1996  Kim et al. .................. 556/418

Primary Examiner—Paul F. Shaver
Attorney, Agent, or Firm—Sughrue, Mion, Zinn, Macpeak & Seas

[57] ABSTRACT

A process for preparing an optically active (2S,3S)-allophenylnorstatin derivative (I) is disclosed, comprising asymmetrically hydrogenating a 4-phenyl-2-halogeno-3-oxobutyric ester (III) in the presence of a ruthenium-phosphine complex to obtain a 4-phenyl-(2S)-halogeno-(3R)-hydroxybutyric ester (IV), epoxidizing the ester (IV) in the presence of a base to obtain a 4-phenyl-(2S,3R)-epoxybutyric ester (V), reacting the ester (V) with a tri(lower alkyl)silylazide or a (lower alkyl)diarylsilylazide in the presence of a Lewis to obtain a (3S)-azido-4-phenyl-(2S)-trisubstituted silyloxybutyric ester (VI), hydrogenolyzing the ester (VI) into a (2S,3S)-allophenylnorstatin derivative (VII), protecting the amino group of the compound (VII), and, if desired, hydrolyzing the compound before or after the amino group protection. Compounds (I) can be obtained at high optical purity safely and in good yield.

7 Claims, No Drawings

PROCESS FOR PREPARING OPTICALLY ACTIVE ALLOPHENYLNORSTATIN DERIVATIVES

FIELD OF THE INVENTION

This invention relates to a process for synthesizing an optically active (2S,3S)-allophenylnorstatin derivative useful as a starting material for synthesizing a peptide compound (KNI-272) which exhibits HIV protease inhibitory activity and is useful as an AIDS remedy, the peptide compound being represented by formula (II):

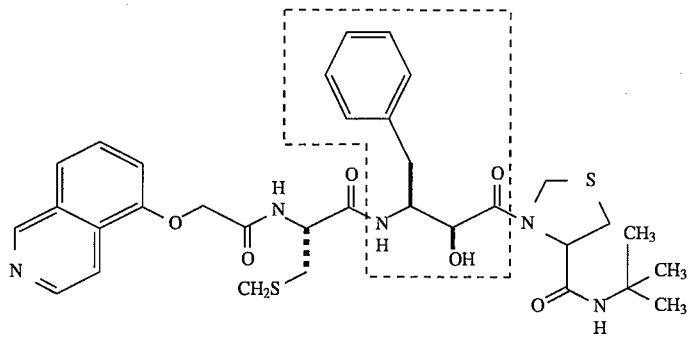

BACKGROUND OF THE INVENTION

The steric configuration of the peptide compound of formula (II) has influences on activity. It is particularly preferred that the two asymmetric carbon atoms in the moiety enclosed with a dotted line in formula (II) are both in an S-configuration.

The steric configuration of the above moiety of the peptide compound of formula (II) depends on the starting compound from which the moiety is derived, i.e., an optically active (2S, 3S)-allophenylnorstatin derivative represented by formula (I):

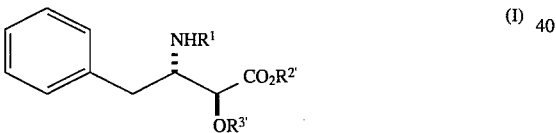

wherein $R^1$ represents an amino group protective group; $R^{2'}$ represents a hydrogen atom or a lower alkyl group; and $R^{3'}$ represents a hydrogen atom, a tri(lower alkyl)silyl group or a (lower alkyl)diarylsilyl group.

It is known that (2S,3S)-allophenylnorstatin can be prepared by a process starting with phenylalanine, which comprises oxidizing an alcohol derived from phenylalanine to form an aldehyde, adding hydrogen cyanide to the aldehyde, and inverting the steric configuration of the hydroxyl groups to provide two optically active sites (see *J. Med. Chem.*, Vol. 33, p. 2707, 1990).

However, industrialization of the above process raises problems because of the involvement of an oxidation reaction, a step of using a harmful cyanide, and a step of steric inversion. In addition, since the intermediate aldehyde is very labile and ready to racemize, it has been very difficult to obtain the desired compound at high optical purity. It has therefore been demanded to develop a process for preparing (2S,3S)-allophenylnorstatin derivatives (I) at high optical purity, easily, safely, and in high yield.

Under the circumstances, the inventors of the present invention have conducted extensive investigations and succeeded in preparing an optically active (2S,3S)-allophenylnorstatin derivative easily, safely and in high yield through novel phenylbutyric acid derivative intermediates derived from a 4-phenyl-2-halogeno-3-oxobutyric acid ester as a starting material, and thus completed the present invention.

The process of the present invention is represented by the following reaction scheme:

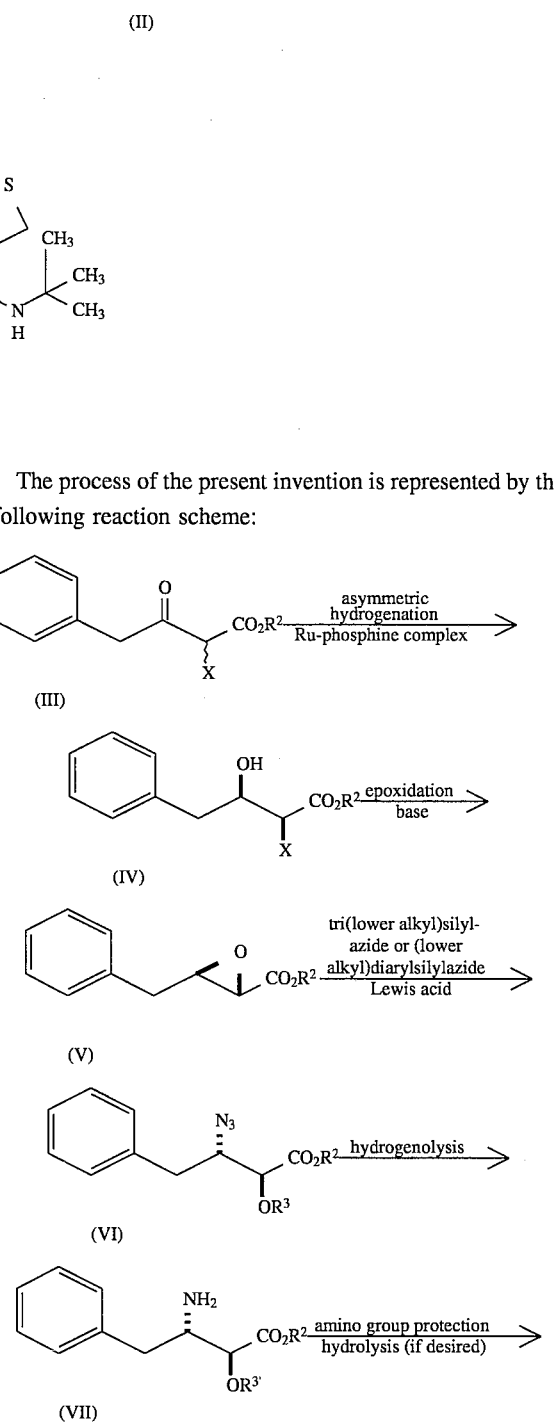

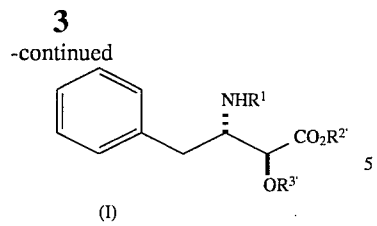

(I)

wherein $R^1$, $R^{2'}$, and $R^{3'}$ are as defined above; $R^2$ represents a lower alkyl group; $R^3$ represents a hydrogen atom, a tri(lower alkyl)silyl group or a (lower alkyl)diarylsilyl group; and X represents a halogen atom.

That is, the present invention provides a process for preparing an optically active (2S,3S)-allophenylnorstatin derivative represented by formula (I), which comprises asymmetrically hydrogenating a 4-phenyl-2-halogeno-3-oxobutyric acid ester represented by formula (III) in the presence of a ruthenium-phosphine complex to obtain a 4-phenyl-(2S)-halogeno-(3R)-hydroxybutyric acid ester represented by formula (IV), epoxidizing the ester (IV) in the presence of a base to obtain a 4-phenyl-(2S,3R)-epoxybutyric acid ester represented by formula (V), reacting the ester of formula (V) with a tri(lower alkyl)silylazide or a (lower alkyl)diarylsilylazide in the presence of a Lewis acid to obtain a (3S)-azido-4-phenyl-(2S)-trisubstituted silyloxybutyric acid ester represented by formula (VI), hydrogenolyzing the ester of formula (VI) into a (2S,3S)-allophenylnorstatin derivative represented by formula (VII), protecting the amino group of the compound of formula (VII), and, if desired, hydrolyzing the compound of formula (VII) before the amino group protection or the compound of formula (VII) after the amino group protection.

SUMMARY OF THE INVENTION

In formulae (I) to (VII), the term "lower alkyl group" includes those having 1 to 6 carbon atoms, such as methyl, ethyl, propyl, isopropyl, butyl, isobutyl and t-butyl groups.

The amino group protective group as represented by $R^1$ includes acetyl, benzyl, benzoyl, t-butoxycarbonyl and benzyloxycarbonyl groups.

The starting material, 4-phenyl-2-halogeno-3-oxobutyric ester (III) is obtained by halogenation of a 4-phenyl-3-oxobutyric ester in a conventional manner (see *J. Org. Chem.*, Vol. 29, p. 1956 (1964)). The halogen atom as represented by X includes chlorine, bromine and iodine atoms.

4-Phenyl-(2S)-halogeno-(3R)-hydroxybutyric ester (IV) is obtained by stereoselective hydrogenation of the compound (III) using a ruthenium-phosphine complex as a catalyst. Examples of the ruthenium-phosphine complex which can be used are shown below.

(a) Complexes represented by formulae (VIII) and (IX), disclosed in JP-A-61-63690 and JP-A-2-191289 (the term "JP-A" as used herein means an "unexamined published Japanese patent application"):

$$Ru_2X_4(R^3\text{—BINAP})_2(NEt_3) \qquad (VIII)$$

$$[RuX(Y)(R^3\text{—BINAP})]X \qquad (IX)$$

wherein $R^3$—BINAP represents a tertiary phosphine ligand represented by formula (X):

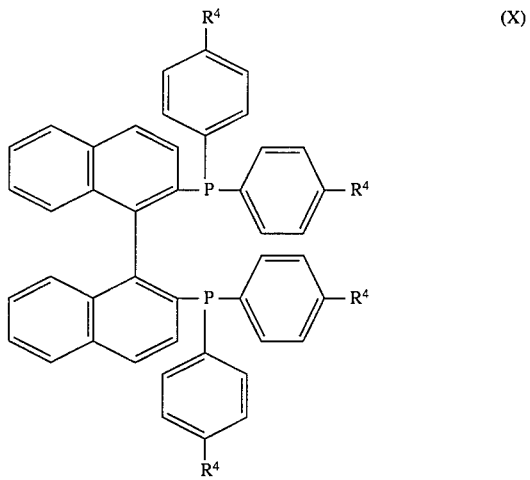

(X)

wherein $R^4$ represents a hydrogen atom, a methyl group, a t-butyl group or a methoxy group;

Et represents an ethyl group; X represents a halogen atom; and Y represents a substituted or unsubstituted phenyl group.

(b) Complexes represented by formulae (XI) and (XII), disclosed in JP-A-4-139140:

$$Ru_2X_4(H_8\text{—BINAP})_2(NEt_3) \qquad (XI)$$

$$[RuX(Y)(H_8\text{—BINAP})]X \qquad (XII)$$

wherein $H_8$—BINAP represents a tertiary phosphine ligand represented by formula (XIII):

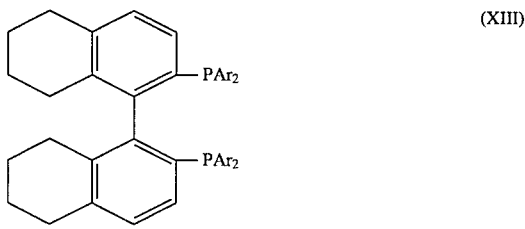

(XIII)

wherein Ar represents a p-methoxyphenyl group, a p-tolyl group, an m-tolyl group, a p-chlorophenyl group, a p-fluorophenyl group, a p-trifluorophenyl group or a 3,5-xylyl group;

and Et, X, and Y are as defined above.

(c) Complexes represented by formula (XIV), disclosed in JP-A-63-135397:

$$Ru_2X_4(R^5\text{—BIPHEMP})_2(NEt_3) \qquad (XIV)$$

wherein $R^5$—BIPHEMP represents a tertiary phosphine ligand represented by formula (XV):

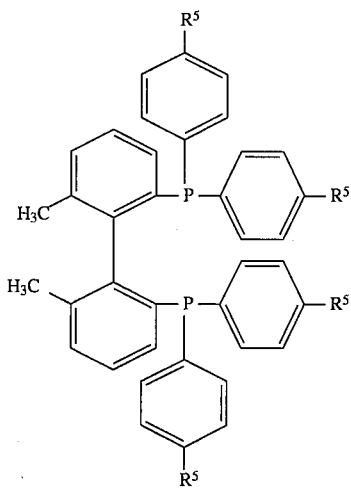

wherein $R^5$ represents a hydrogen atom, a methyl group or a methoxy group;
and Et and X are as defined above.

(d) Complexes represented by formulae (XVI) and (XVII), disclosed in JP-B-6-92427 (the term "JP-B" as used herein means an "examined Japanese patent publication"):

$$Ru_2X_4(BICHEP)_2(NEt_3) \quad (XVI)$$

$$[RuX(Y)(BICHEP)]X \quad (XVII)$$

wherein BICHEP represents a tertiary phosphine ligand represented by formula (XVIII):

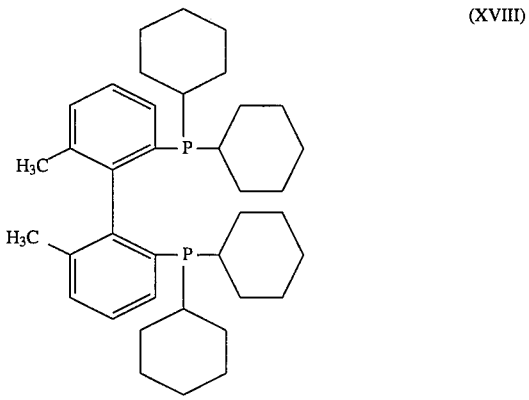

and Et, X, and Y are as defined above.

Additional examples of optically active phosphines which can be used as a ligand of the ruthenium-phosphine complex are (4,4',6,6'-tetramethyl-5,5'-dimethoxybiphenyl-2,2'-diyl)-bis(diphenylphosphine) and (4,4',6,6'-tetramethyl-5,5'-dimethoxybiphenyl-2,2'-diyl)-bis(di-p-methoxyphenylphosphine) described in *Chem. Pharm. Bull.*, Vol. 39, p. 1085 (1991); (4,4',6,6'-tetratrifluoromethyl-5,5'-dimethoxybiphenyl-2,2'-diyl)-bis(diphenylphosphine) and (4,6-ditrifluoromethyl-4',6'-dimethyl-5'-methoxybiphenyl-2,2'-diyl)-bis-(diphenylphosphine) described in *Synlett.*, p. 827 (1991); 2-dicyclohexyl-2'-diphenylphosphino-4,4',6,6'-tetramethyl-5,5'-dimethoxybiphenyl-2,2'-diyl)-bis(diphenylphosphine) described in *Tetrahedron: Asymmetry*, Vol. 3, p. 13 (1992); (6,6'-dimethyl-2,2'-biphenylene)-bis(diphenylphosphine), (4,4',6,6'-tetramethyl-2,2'-biphenylene)-bis(diphenylphosphine), (3,3',6,6'-tetramethyl-2,2'-biphenylene)-bis(diphenylphosphine), (4,4'-difluoro-6,6'-dimethyl-2,2'-biphenylene)-bis(diphenylphosphine), (4,4'-bis(dimethylamino)-6,6'-dimethyl-2,2'-biphenylene)-bis(diphenylphosphine), (6,6'-dimethyl-2,2'-biphenylene)-bis(di-p-tolylphosphine), (6,6'-dimethyl-2,2'-biphenylene)-bis(di-o-tolylphosphine), (6,6'-dimethyl-2,2'-biphenylene)-bis(di-m-fluorophenylphosphine), and 1,11-bis(diphenylphosphino)-5,7-dihydrodibenzo[c,e]oxepin, disclosed in JP-B-4-15796; and (6,6'-dimethoxybiphenyl-2,2'-diyl)-bis(diphenylphosphine), (5,5',6,6'-tetramethoxybiphenyl-2,2'-diyl)-bis(diphenylphosphine), (6,6'-dimethoxybiphenyl-2,2'-diyl)-bis(di-p-tolylphosphine), and (4,4',5,5',6,6'-hexamethoxybiphenyl-2,2'-diyl)-bis(diphenylphosphine) disclosed in JP-A-3-5492.

The ruthenium-phosphine complex is preferably used in an amount of 0.0002 to 0.02 mol, particularly preferably of 0.001 to 0.01 mol, per mole of compound (III). Generally employed organic solvents, such as methanol, ethanol, 1-propanol, 2-propanol, 1-butanol, 2-methyl-2-propanol, methylene chloride, tetrahydrofuran (hereinafter abbreviated as THF), and toluene, and mixtures thereof can be used in the asymmetric hydrogenation reaction. The solvents mentioned above can be used in the subsequent reactions similarly. In this reaction, the solvent is preferably used in an amount 2 to 10 times the volume of compound (III).

The reaction is carried out at 0° to 150° C., preferably 20° to 100° C., under a hydrogen pressure of 10 to 150 atm, preferably 30 to 100 atm, preferably for a period of 1 to 30 hours. The reaction product may be purified by, for example, silica gel column chromatography, but can be subjected as produced to the subsequent reaction.

4-Phenyl-(2S,3R)-epoxybutyric ester (V) is obtained by epoxidizing compound (IV) through reaction with a base. The epoxidation reaction is carried out at, e.g., −20° to 30° C., preferably −5° to 5° C., for 1 to 3 hours. Suitable bases include alkali alkoxides, such as sodium methylate, sodium ethylate, sodium propylate, sodium isopropylate, sodium butyrate, sodium t-butylate, potassium methylate, potassium ethylate, potassium propylate, potassium isopropylate, potassium butylate, and potassium t-butylate. A solvent is preferably used in an amount 1 to 3 times the volume of compound (IV). After the reaction, the reaction product can be purified by adding a phosphate buffer (pH 7.0) to the reaction mixture, removing the solvent by evaporation, extracting the residue with toluene, ethyl acetate, diethyl ether, methylene chloride, chloroform, etc., removing the extracting solvent by evaporation, and distilling the extract.

(3S)-Azido-4-phenyl-(2S)-butyric ester (VI) is obtained by reacting compound (V) with a tri(lower alkyl)silylazide or a (lower alkyl)diarylsilylazide in the presence of a Lewis acid. The tri(lower alkyl)silylazide includes trimethylsilylazide, triethylsilylazide, tripropylsilylazide, triisopropylsilylazide, tributylsilylazide, triisobutylsilylazide, tri(sec-butyl)silylazide, tri(t-butyl)silylazide, t-butyldimethylsilylazide, and dimethylhexylsilylazide. The (lower alkyl)diarylsilylazide includes t-butyldiphenylsilylazide. The Lewis acid includes zinc chloride, zinc bromide, titanium tetrachloride, titanium tetrabromide, aluminum chloride, aluminum bromide, titanium tetraisopropoxide, aluminum triisopropoxide, tin dichloride, and tin tetrachloride. The tri(lower alkyl)silylazide or (lower alkyl)diarylsilylazide is preferably used in an amount of 1 to 1.2 mol per mole of compound (IV), and the Lewis acid is preferably used in an amount of 1 to 20 mol % based on compound (IV). The reaction temperature preferably ranges from 50° to 100° C. The reaction can be carried out in the absence or presence of a solvent, such as benzene, toluene, xylene, diethyl ether, THF, dimethoxyethane, methylene chloride, ethyl acetate, methyl acetate, butyl acetate, and 1,2-dichloroethane. Purification can be conducted by, for example, silica gel column chromatography.

Optically active (2S,3S)-allophenylnorstatin derivative (VII) is obtained by hydrogenolysis of compound (VI) using 1 to 10% by weight, based on compound (VI), of a catalyst, such as 5 to 10% palladium-on-carbon. The reaction is carried out at 0° to 100° C., preferably 20° to 50° C., under a hydrogen pressure of 1 to 50 atm, preferably 10 to 30 atm, for 10 to 40 hours. While not limiting, a solvent is used in an amount 3 to 5 times the volume of compound (VI). Where an alcohol, such as methanol, ethanol, 1-propanol or 2-propanol, is used as a solvent, the tri(lower alkyl)siloxy group at the 2-position is converted to a hydroxyl group. Such conversion does not occur in using THF, dioxane, ethyl acetate, methyl acetate, etc. as a solvent. After the reaction, purification can be carried out by removing the catalyst, evaporating the solvent, and subjecting the residue to, e.g., silica gel column chromatography.

Compound (I) can be obtained by protecting the amino group of compound (VII). The reaction can be achieved by using compounds generally used to provide a protective group for an amino group, such as t-butoxycarbonyl (hereinafter abbreviated as Boc) anhydride, a benzyl halide, an acetyl halide, a benzoyl halide, and a carbobenzoxy halide. The protective group-forming compound is used in an equimolar amount to compound (VII) and added to compound (VII) at 0° to 10° C. as dissolved in a 3 to 5-fold volume of an organic solvent, such as THF or dioxane. After allowing the mixture to react at room temperature for 5 to 20 hours, the solvent is evaporated under reduced pressure, and the residue is extracted with an organic solvent, e.g., ethyl acetate, methyl acetate or butyl acetate. The extracting solvent is removed by evaporation to give compound (I). Purification can be effected by, for example, recrystallization using a 5 to 20-fold volume of a solvent, such as ethyl acetate.

The compound of formula (I) in which $R^{2'}$ and/or $R^{3'}$ is/are hydrogen is obtained by hydrolysis before or after the amino group protection. The hydrolysis reaction can be carried out by dissolving compound (VII) or compound (I) (wherein at least one of $R^{2'}$ and $R^{3'}$ is not a hydrogen atom) in a 2 to 5-fold volume of a 1 to 5N sodium hydroxide aqueous solution and allowing the solution to react at 0° to 20° C. overnight. Where compound (VII) is hydrolyzed, it is recommended to use the product as such in the synthesis of compound (I) without being isolated. In some hydrolysis reactions, the ester linkage of compound (VII) also undergoes hydrolysis.

The present invention will now be illustrated in greater detail by way of Examples, but it should be understood that the present invention is not construed as being limited thereto. In Examples the following analytical instruments were used.

$^1$H-NMR: AM-400, manufactured by Bruker Inc.

Specific rotation: DIP-4, manufactured by Nippon Bunko K.K.

Melting point: Micro melting apparatus, manufactured by Yanako K.K.

High performance liquid chromatography (HPLC): SPD10A, LC10AT, manufactured by Shimadzu Corporation Gas chromatography (GC): 5890II, manufactured by Hewlett Packard

EXAMPLE 1

(1) Synthesis of Methyl 4-Phenyl-3-oxobutyrate:

In 70 ml of methylene chloride was dissolved 36.03 g (0.25 mol) of Meldrum's acid. Pyridine (38.17 g, 0.48 mol) was used as a base. To the solution was added dropwise 42.52 g (0.275 mol) of phenylacetyl chloride in an ice bath while stirring. After the reaction, ice-water and diluted hydrochloric acid were added to wash. Methylene chloride was evaporated, methanol was added, followed by refluxing, and the solvent was evaporated to give 44 g (91.7%) of methyl 4-phenyl-3-oxobutyrate.

(2) Synthesis of Methyl 4-Phenyl-2-chloro-3-oxobutyrate (compound (III)):

Methyl 4-phenyl-3-oxobutyrate (44 g, 0.229 mol) obtained in (1) above was cooled (with no solvent) in an ice bath, and 30.93 g (0.229 mol) of sulfuryl chloride was added dropwise, followed by stirring overnight. Excess sulfuryl chloride was evaporated under reduced pressure, and the residue was dissolved in toluene and washed with an aqueous solution of sodium hydrogencarbonate. The solvent was removed by evaporation, and the residue was purified by silica gel column chromatography to obtain 45.68 g of the title compound (III) in a yield of 88.0%.

(3) Synthesis of Methyl (2S,3R)-2-chloro-3-hydroxy-4-phenylbutyrate (compound (IV)):

In a 500 ml Schlenk tube was put 0.36 g (0.4 mmol) of $Ru_2Cl_4((R)$-tol—$BINAP)_2(NEt_3)$. After purging with nitrogen, 56.7 g (0.2 mmol) of methyl 4-phenyl-2-chloro-3-oxobutyrate (compound (III)) and 280 ml of methanol were dissolved therein. The solution was charged in a 500 ml autoclave and stirred at room temperature under a hydrogen pressure of 80 atm for 20 hours. The reaction mixture was concentrated to give 57.2 g (95%) of the title compound (IV).

Analysis by HPLC (Inertsil SIL; hexane:THF=95.5 by volume) revealed that the diastereomer ratio (syn:anti) was 63:37.

Analysis by HPLC (CHIRALCEL OD-H; hexane:2-propanol=99:1 by volume) revealed the optical purity of 74% ee (syn) and 70% ee (anti).

$^1$H-NMR (CDCl$_3$) δppm:

syn: 2.47 (brs, 1H), 2.86 (d, d, J=14.0, 6.3Hz, 1H), 3.12 (d, d, J=13.9, 10.1Hz, 1H), 3.80 (s, 3H), 4.18 (d, J=7.3Hz), 4.27 (brs, 1H), 7.26–7.33 (m, 5H)

anti: 2.62 (brs, 1H), 2.90 (d, d, J=13.0, 3.9Hz, 1H), 2.99 (d, d, J=13.0, 9.8Hz, 1H), 3.78 (s, 3H), 4.27 (d, J=3.1Hz, 1H), 4.21–4.30 (brs, 1H), 7.26–7.33 (m, 5H)

Alternatively, the following process may be used to synthesize compound (IV).

In a 200 ml Hastelloy autoclave was put 50 g (GC p=93.2%, 220 mmol) of methyl 4-phenyl-2-chloro-3-oxobutyrate (compound (III)), 99.4 mg (0.055 mmol) of $Ru_2Cl_4[(R)$-T-$BINAP]_2NEt_3$, and 100 ml of isopropyl alcohol (IPA) under a nitrogen stream. After heating the solution, a hydrogen pressure of 30 atm was introduced into the autoclave at 100° C. to initiate the reaction. Then, it was confirmed by GC that no unreacted matter remained to complete the reaction (for 1 to 2 hours). IPA was recovered under reduced pressure at not higher than 50° C. to obtain 50.3 g [GC p=92.2%, HPLC o.p. syn 87% (80.5% ee), anti 13% (94.6% ee)] of compound (IV) in a yield of 98.6%.

Analysis by GC: HP 5890A
  Column: Neutra bond 1 30 m×0.25 mm
  Temp.: 100°–220° C., 5° C./min Analysis by HPLC:
  Column: CHIRALCEL OD-H
  Solvents: n-Hexane/IPA=99/1 (by volume)
  Detector: UV detector 254 nm
  Flow rate: 1.0 ml/min (4) Synthesis of Methyl (2S,3R)-2,3-Epoxy-4-phenylbutyrate (compound (V)):

In a reaction container were put 59.4 g (0.275 mol) of a 28% methanol solution of sodium methylate and 60 ml of methanol. To the mixture was added dropwise a solution of 57.2 g (0.25 mol) of methyl (2S,3R)-2-chloro-3-hydroxy-4-phenylbutyrate (compound (IV)) in 120 ml of methanol under cooling in an ice bath, followed by stirring at that temperature for 2 hours. A 0.1M phosphate buffer (pH=7; 280 ml) was cooled in an ice bath, and the reaction solution was slowly poured therein. Methanol was evaporated under reduced pressure, and the residue was extracted with ethyl acetate. The extract was washed with brine. The solvent was evaporated, and the residue was subjected to simple distillation to recover 31.5 g (75%) of the title compound (V).

Boiling point: 105° C. (0.3 Torr) Gas-liquid chromatography (GLC) (Neutrabond-1, 100 to 250° C., 5° C./min) revealed a trans:cis ratio of >99:1.

$^1$H-NMR (CDCl$_3$) δppm: 2.96 (d, J=5.3Hz, 2H), 3.28 (d, J=1.8Hz, 1H), 3.40–3.42 (m, 1H), 3.76 (s, 3H), 7.23–7.32 (m, 5H)

(5) Synthesis of Methyl (2S,3S)-2-Trimethylsiloxy-3-azido-4-phenylbutyrate (compound (VI)):

In a reaction container were charged 31.5 g (0.164 mol) of methyl (2S,3R)-2,3-epoxy-4-phenylbutyrate (compound (V)), 23.1 g (0.18 mol) of azidotrimethylsilane, and 2.24 g (16 mmol) of zinc chloride and stirred at 70° C. for 20 hours. If an HPLC analysis showed that the reaction had not completed, an additional amount of zinc chloride was added. The reaction mixture was poured into 100 ml of toluene and 50 g of silica gel and stirred for 1 hour, followed by filtration. The filtrate was washed with toluene and concentrated. The concentrate was purified by silica gel column chromatography (500 g, hexane:ethyl acetate=95:5 by volume) to give 39.8 g (79.1%) of the title compound (VI).

$^1$H-NMR (CDCl$_3$) δppm: 0.19 (s, 9H), 2.90–2.95 (m, 2H), 3.70 (s, 3H), 3.76–3.79 (m, 1H), 4.34 (d, J=4.1Hz, 1H), 7.23–7.30 (m, 5H)

Alternatively, the following process may be used to synthesize compound (VI).

A mixture of 92.4 g (GC p=94.5%, 454 mmol) of methyl (2S,3R)-2,3-epoxy-4-phenylbutyrate(compound (V)), 60.6 g (0.5 mol, 1.1 eq) of 95% TMS-N$_3$, and 4.37 g (23 mmol) of SnCl$_2$ was stirred under heating, and reacted for 12 hours at 70° C. Heating was continued until 99% or more conversion was confirmed by GC. Then, 280 ml of toluene was added to the mixture, and further 92.4 g of silicagel was added at not higher than 30° C. with stirring for 1 hour. After filtration and washing with 280 ml of toluene, toluene was recovered at not higher than 50° C. to obtain 130.6 g (GC p=76.9%, i.e., pure amount 100.4 g) of compound (VI) in a yield of 71.9%.

Analysis by GC: HP 5890A
Column: Neutra bond 1 30 m×0.25 mm
Temp.: 100°–220° C., 5° C./min (6) Synthesis of (2S,3S)-2-Hydroxy-3-t-butoxycarbonylamino-4-phenylbutyric Acid (Boc-AHPBA-OH) (compound (I)):

In a 500 ml autoclave were charged 41.7 g (0.136 mol) of methyl (2S,3S)-2-trimethylsiloxy-3-azido-4-phenylbutyrate (compound (VI)), 2 g of 5% palladium carbon, and 200 ml of THF, and the mixture was stirred at 50° C. under a hydrogen pressure of 20 atm for 20 hours. The catalyst was removed by filtration using Celite, and the solvent was removed by evaporation under reduced pressure. The residue (36.2 g) was cooled in an ice-bath, and 200 ml (1.5 eq.) of 1N sodium hydroxide was added thereto, followed by stirring at room temperature overnight. To the reaction mixture were added dropwise 32.6 g (0.146 mol) of Boc anhydride and 135 ml of THF in an ice bath, and the mixture was stirred at room temperature overnight. The organic solvent was evaporated under reduced pressure, and the residual aqueous layer was washed with 100 ml of toluene. To the aqueous layer was added 100 ml of ethyl acetate, and the mixture was neutralized to pH 4 to 5 with 20% phosphoric acid while stirring under cooling with ice. The ethyl acetate layer was taken out, and the solvent was evaporated under reduced pressure to obtain 34 g (85%) of the desired compound. Recrystallization from a 15-fold volume of ethyl acetate gave 17 g (50%) of the title compound.

Melting point: 147°–148° C.

$[α]_D^{24}$: 0.20° (c=1.00, CH$_3$OH)

$^1$H-NMR (CDCl$_3$) δppm (compound (VII); R$^3$'=trimethylsilyl (TMS)): 0.28 (s, 9H), 2.61 (d, d, J=13.6, 4.1Hz, 1H), 3.03 (d, d, J=13.6, 9.3Hz, 1H), 3.85 (s, 3H), 4.25 (d, J=5.0Hz, 1H), 7.31–7.42 (m, 5H)

$^1$H-NMR (CD$_3$OD) δppm (compound (I); R$^1$=Boc): 1.31 (s, 9H), 2.69–2.81 (m, 2H), 4.11–4.16 (m, 1H), 4.18–4.20 (m, 1H), 7.12–7.25 (m, 5H)

Alternatively, the following process may be used to synthesize compound (I).

In an autoclave was put 130.6 g (GC p=76.9%, 100.4 g, 327 mmol) of compound (VI), 71.2 g (327 mmol) of Boc$_2$O, 5.0 g (5% wt) of 5% Pd-C, and 400 ml of IPA under a nitrogen stream. A hydrogen pressure of 30 atm was introduced into the autoclave, and reaction was conducted at room temperature for 6 hours. Then, it was confirmed by GC that no unreacted matter remained and thereafter catalyst was separated from the solution by filtration. IPA was recovered under reduced pressure at not higher than 50° C. to obtain 152.1 g (GC p=73.4%, 111.6 g) of (2S,3S)-methyl 3-N-t-butoxycarbonylamino-2-trimethylsilyloxy-4-phenylbutyrate (compound (VII)) in a yield of 89.6%. 152.1 g (GC p=73.4%, 111.6 g, 0.292 mol) of compound (VII) was dissolved in 600 ml of methanol and the solution was stirred under cooling with ice. Then, 440 ml (0.44 mol) of 1N NaOH was dropped thereinto at not higher than 10° C. After stirring for 2 hours at room temperature, methanol was recovered under reduced pressure, and the residual aqueous layer was washed with 150 ml of toluene. Then, 330 ml of ethyl acetate was added to the aqueous layer, and the mixture was neutralized to pH 5 with 20% HCl. After separation treatment, the aqueous layer was extracted with 330 ml of ethyl acetate, and the solvents including the ethyl acetate were recovered under reduced pressure. 660 ml of a mixed solvent of ethyl acetate/toluene (1:2) was further added to the solution and heat dissolved at 50° C., low-temperature crystallization was conducted. Then, filtration was conducted at −15° C. to obtain 42.3 g of compound (I) (p=98.0%, m.p. 147°–148° C.). Further, 13.8 g of secondary crystal was obtained from the mother liquor (p=95.0%, m.p. 143°–146° C.). Yield, 65.0%.

Analysis by GC: HP 5890A
Column: Neutra bond 1 30 m×0.25 mm
Temp.: 100°–220° C., 5° C./min
HPLC: (Chemical purity)
Column: Inertsil ODS-2 4.6 mm×250 mm
Solvents: CH$_3$CN/H$_2$O=4/6 (pH=2.3 H$_3$PO$_4$)
Flow rate: 0.5 ml/min
Detector: UV detector 230 nm
Column temp.: 35° C. (Optical purity)
Column: TSK gel Enantio L1 4.6 mm×250 mm (TOSOH)
Solvents: 1 mM CuSO$_4$ aq/MeOH=95/5
Flow rate: 0.7 ml/min
Detector: UV detector 254 nm

What is claimed is:

1. A process for preparing an optically active (2S,3S)-allophenylnorstatin derivative represented by formula (I):

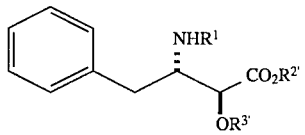

wherein $R^1$ represents an amino group protective group; $R^{2'}$ represents a hydrogen atom or a lower alkyl group; and $R^{3'}$ represents a hydrogen atom, a tri(lower alkyl)silyl group or a (lower alkyl)diarylsilyl group; which comprises the steps of:

asymmetrically hydrogenating a 4-phenyl-2-halogeno-3-oxobutyric acid ester represented by formula (III):

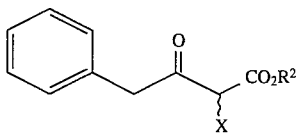

wherein $R^2$ represents a lower alkyl group; and X represents a halogen atom;

in the presence of a ruthenium-phosphine complex to obtain a 4-phenyl-(2S)-halogeno-(3R)-hydroxybutyric acid ester represented by formula (IV):

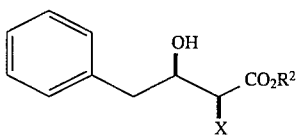

wherein $R^2$ and X are as defined above;

epoxidizing the ester represented by formula (IV) in the presence of a base to obtain a 4-phenyl-(2S,3R)-epoxybutyric acid ester represented by formula (V):

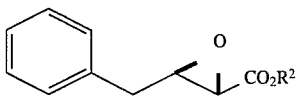

wherein $R^2$ is as defined above;

reacting the ester represented by formula (V) with a tri(lower alkyl)silylazide or a (lower alkyl)diarylsilylazide in the presence of a Lewis acid to obtain a (3S)-azido-4-phenyl-(2S)-trisubstituted silyloxybutyric acid ester represented by formula (VI):

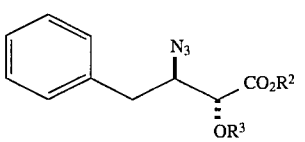

wherein $R^2$ is as defined above; and $R^3$ represents a hydrogen atom, a tri(lower alkyl)silyl group or a (lower alkyl)diarylsilyl group;

hydrogenolyzing the ester represented by formula (VI) to obtain a (2S,3S)-allophenylnorstatin derivative represented by formula (VII):

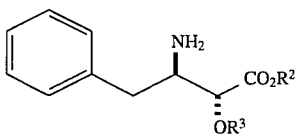

wherein $R^2$ and $R^{3'}$ are as defined above;

protecting the amino group of the compound represented by formula (VII), and, if desired, hydrolyzing the compound before or after the amino group protection.

2. The process as claimed in claim 1, wherein said ruthenium-phosphine complex used in the asymmetrically hydrogenating step is selected from the group consisting of complexes represented by formulae (VIII), (IX), (XI), (XII), (XIV), (XVI) and (XVII):

| | |
|---|---|
| $Ru_2X_4(R^3\text{—BINAP})_2(NEt_3)$ | (VIII) |
| $[RuX(Y)(R^3\text{—BINAP})]X$ | (IX) |
| $Ru_2X_4(H_8\text{—BINAP})_2(NEt_3)$ | (XI) |
| $[RuX(Y)(H_8\text{—BINAP})]X$ | (XII) |
| $Ru_2X_4(R^5\text{—BIPHEMP})_2(NEt_3)$ | (XIV) |
| $Ru_2X_4(BICHEP)_2(NEt_3)$ | (XVI) |
| $[RuX(Y)(BICHEP)]X$ | (XVII) | wherein $R^3$—BINAP represents a tertiary phosphine ligand represented by formula (X):

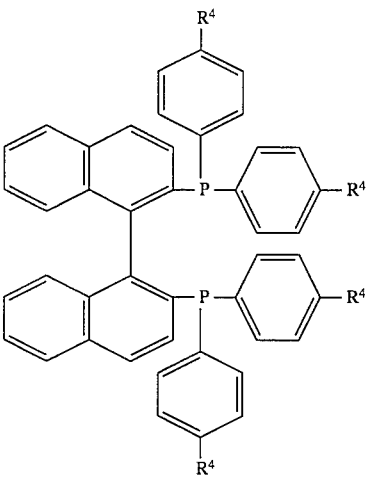

wherein $R^4$ represents a hydrogen atom, a methyl group, a t-butyl group or a methoxy group;

Et represents an ethyl group; X represents a halogen atom; Y represents a substituted or unsubstituted phenyl group; $H_8$—BINAP represents a tertiary phosphine ligand represented by formula (XIII):

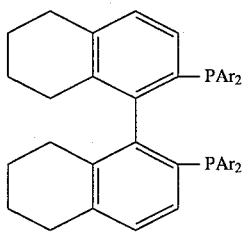

(XIII)

wherein Ar represents a p-methoxyphenyl group, a p-tolyl group, an m-tolyl group, a p-chlorophenyl group, a p-fluorophenyl group, a p-trifluorophenyl group or a 3,5-xylyl group;

$R^5$—BIPHEMP represents a tertiary phosphine ligand represented by formula (XV):

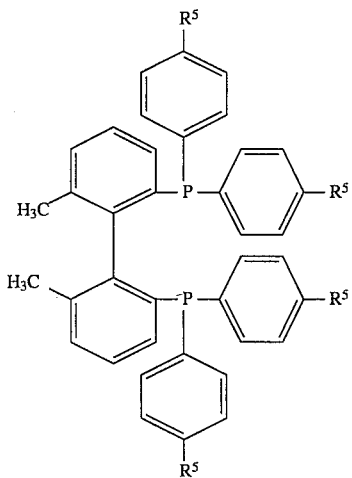

(XV)

wherein $R^5$ represents a hydrogen atom, a methyl group or a methoxy group;

and BICHEP represents a tertiary phosphine ligand represented by formula (XVIII):

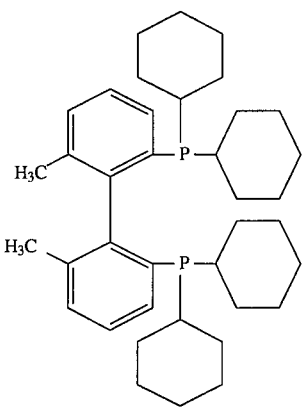

(XVIII)

3. The process as claimed in claim 1, wherein said ruthenium-phosphine complex is used in an amount of 0.0002 to 0.02 mol per mole of compound (III).

4. The process as claimed in claim 1, wherein said ruthenium-phosphine complex is used in an amount of 0.001 to 0.01 mol per mole of compound (III).

5. The process as claimed in claim 1, wherein said base used in the epoxidizing step is selected from the group consisting of sodium methylate, sodium ethylate, sodium propylate, sodium isopropylate, sodium butyrate, sodium t-butylate, potassium methylate, potassium ethylate, potassium propylate, potassium isopropylate, potassium butylate, and potassium t-butylate.

6. The process as claimed in claim 1, wherein said Lewis acid is selected from the group consisting of zinc chloride, zinc bromide, titanium tetrachloride, titanium tetrabromide, aluminum chloride, aluminum bromide, titanium tetraisopropoxide, aluminum triisopropoxide, tin dichloride, and tin tetrachloride.

7. The process as claimed in claim 1, wherein said tri(lower alkyl)silylazide or (lower alkyl)diarylsilylazide is used in an amount of 1 to 1.2 mol per mole of compound (IV), and said Lewis acid is used in an amount of 1 to 20 mol % based on compound (IV).

* * * * *